(12) United States Patent
Bergin

(10) Patent No.: US 8,273,118 B2
(45) Date of Patent: Sep. 25, 2012

(54) HEART VALVE HOLDER ASSEMBLY FOR USE IN VALVE IMPLANTATION PROCEDURES

(75) Inventor: Cathleen A. Bergin, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 991 days.

(21) Appl. No.: 12/283,890

(22) Filed: Sep. 16, 2008

(65) Prior Publication Data

US 2009/0076599 A1 Mar. 19, 2009

Related U.S. Application Data

(60) Provisional application No. 60/994,063, filed on Sep. 17, 2007.

(51) Int. Cl.
*A61F 2/24* (2006.01)
(52) U.S. Cl. ...................................................... 623/2.11
(58) Field of Classification Search ................. 623/2.11, 623/2.38–2.41; 606/139, 151
See application file for complete search history.

(56) References Cited

U.S. PATENT DOCUMENTS

| | | |
|---|---|---|
| 3,099,016 A | 7/1963 | Edwards |
| 3,197,788 A | 8/1965 | Segger |
| 3,263,239 A | 8/1966 | Edwards et al. |
| 3,365,728 A | 1/1968 | Edwards et al. |
| 3,466,671 A | 9/1969 | Siposs |
| 3,509,582 A | 5/1970 | Pierie |
| 3,534,410 A | 10/1970 | Raible |
| 3,570,014 A | 3/1971 | Hancock |
| 3,656,185 A | 4/1972 | Carpentier |
| 3,710,744 A | 1/1973 | Goodenough et al. |
| 3,714,671 A | 2/1973 | Edwards et al. |
| 3,723,996 A | 4/1973 | Raible et al. |
| 3,755,823 A | 9/1973 | Hancock |
| 4,084,268 A | 4/1978 | Ionescu et al. |
| 4,106,129 A | 8/1978 | Carpentier et al. |
| 4,259,753 A | 4/1981 | Liotta et al. |
| 4,291,420 A | 9/1981 | Reul |
| 4,297,749 A | 11/1981 | Davis et al. |
| 4,327,880 A * | 5/1982 | Dorbandt .................... 242/318 |
| 4,343,048 A | 8/1982 | Ross et al. |
| 4,388,735 A | 6/1983 | Ionescu et al. |
| 4,451,936 A | 6/1984 | Carpentier et al. |
| 4,470,157 A | 9/1984 | Love |
| 4,501,030 A | 2/1985 | Lane |
| 4,626,255 A | 12/1986 | Reichart et al. |
| 4,629,459 A | 12/1986 | Ionescu et al. |
| 4,725,274 A | 2/1988 | Lane et al. |
| 4,778,461 A | 10/1988 | Pietsch et al. |

(Continued)

FOREIGN PATENT DOCUMENTS

EP 0084395 8/1986

(Continued)

OTHER PUBLICATIONS

U.S. Appl. No. 60/117,445, filed Jan. 26, 1999, Carpentier et al.

(Continued)

*Primary Examiner* — Corrine M McDermott
*Assistant Examiner* — Gregory Anderson (57) ABSTRACT

A valve holder assembly for delivering a prosthetic heart valve having a stent base an multiple extending commissure posts. The valve holder assembly includes a holder and a rotor that is rotatable relative to the holder.

20 Claims, 6 Drawing Sheets

U.S. PATENT DOCUMENTS

| | | | | |
|---|---|---|---|---|
| 4,851,000 | A | 7/1989 | Gupta | |
| 4,865,600 | A | 9/1989 | Carpentier et al. | |
| 5,147,391 | A | 9/1992 | Lane | |
| 5,163,953 | A | 11/1992 | Vince | |
| 5,163,955 | A | 11/1992 | Love et al. | |
| 5,258,023 | A | 11/1993 | Reger | |
| 5,411,552 | A | 5/1995 | Andersen et al. | |
| 5,449,384 | A | 9/1995 | Johnson | |
| 5,476,510 | A | 12/1995 | Eberhardt et al. | |
| 5,489,297 | A | 2/1996 | Duran | |
| 5,489,298 | A | 2/1996 | Love et al. | |
| 5,500,016 | A | 3/1996 | Fisher | |
| 5,549,665 | A | 8/1996 | Vesely et al. | |
| 5,554,185 | A | 9/1996 | Block et al. | |
| 5,697,382 | A | 12/1997 | Love et al. | |
| 5,702,368 | A | 12/1997 | Stevens et al. | |
| 5,716,401 | A | 2/1998 | Eberhardt et al. | |
| 5,716,417 | A | 2/1998 | Girard et al. | |
| 5,728,152 | A | 3/1998 | Mirsch, II et al. | |
| 5,800,527 | A | 9/1998 | Jansen et al. | |
| 5,800,531 | A | 9/1998 | Cosgrove et al. | |
| 5,855,601 | A | 1/1999 | Bessler et al. | |
| 5,861,028 | A | 1/1999 | Angell | |
| 5,895,420 | A | 4/1999 | Mirsch, II et al. | |
| 5,928,281 | A | 7/1999 | Huynh et al. | |
| 5,935,163 | A | 8/1999 | Gabbay | |
| 5,964,770 | A | 10/1999 | Flomenblit et al. | |
| 6,019,790 | A | 2/2000 | Holmberg et al. | |
| 6,074,419 | A | 6/2000 | Healy et al. | |
| 6,102,845 | A | 8/2000 | Woodard et al. | |
| 6,338,740 | B1 | 1/2002 | Carpentier | |
| 6,409,758 | B2 | 6/2002 | Stobie et al. | |
| 6,558,418 | B2 | 5/2003 | Carpentier et al. | |
| 6,702,852 | B2 | 3/2004 | Stobie et al. | |
| 6,719,785 | B2 | 4/2004 | Schoon et al. | |
| 6,736,845 | B2 | 5/2004 | Marquez et al. | |
| 6,964,682 | B2 | 11/2005 | Nguyen-Thien-Nhon et al. | |
| 6,966,925 | B2 | 11/2005 | Stobie | |
| 7,033,390 | B2 | 4/2006 | Johnson et al. | |
| 7,566,339 | B2 * | 7/2009 | Fallin et al. | 606/232 |
| 2002/0082686 | A1 | 6/2002 | Nguyen-Thien-Nhon | |
| 2003/0125805 | A1 | 7/2003 | Johnson et al. | |
| 2004/0024451 | A1 | 2/2004 | Johnson et al. | |
| 2004/0059413 | A1 | 3/2004 | Argento | |
| 2004/0138741 | A1 | 7/2004 | Stobie et al. | |
| 2004/0148017 | A1 | 7/2004 | Stobie | |
| 2004/0148018 | A1 | 7/2004 | Carpentier et al. | |
| 2006/0241743 | A1 * | 10/2006 | Bergin et al. | 623/2.11 |

FOREIGN PATENT DOCUMENTS

| | | |
|---|---|---|
| EP | 0515324 | 12/1996 |
| GB | 2011259 A | 7/1979 |
| GB | 2108393 | 5/1983 |
| GB | 2279134 | 12/1994 |
| RU | 1806696 | 4/1993 |
| WO | 90/11738 | 10/1990 |
| WO | 92/12690 | 8/1992 |
| WO | 93/18721 | 9/1993 |
| WO | 95/28899 | 11/1995 |
| WO | 97/46177 | 12/1997 |
| WO | 98/43556 | 10/1998 |
| WO | 00/64382 | 4/1999 |
| WO | 00/00107 | 1/2000 |
| WO | 00/42950 | 7/2000 |
| WO | 00/67661 | 11/2000 |
| WO | 02/49545 | 6/2002 |

OTHER PUBLICATIONS

Bernhard et al., "A 'Semi-Supported' Porcine Xenograft—Description and First Clinical Use," Thorac. Cardiovas. Surgeon 37 (1989) pp. 313-315.

Krucinski et al., "Numerical Simulation of Leaflet Flexure in Bioprosthetic Valves Mounted on Rigid and Expansile Stents," J. Biomechanics, vol. 26, No. 8 (1993) pp. 929-943.

Jansen et al., "New J-3 flexible-leaflet polyurethane heart valve prosthesis with improved hydrodynamic performance," International Journal of Artificial Organs, vol. 14 No. 10 (1991) pp. 655-660.

Wright JM et al., Hancock II—An Improved Bioprosthesis. In: Cohn LJ, Galucci V. ed. Cardiac Bioprosthesis. New York, NY: New York Medical Books, 1982.

Hancock® II Bioprosthesis, Clinical Compendium, Copyright 2003, Medtronic, Inc.

Bortolotti et al., "Porcine Valve Durability: A Comparison Between Hancock Standard and Hancock II Bioprostheses," Ann Thorac Surg 60:S216-20 (1995).

John S. T. Masterson, Robert T. Miyigashia, Peter Allen, A Ian Munro and William G. Trapp, Universal Cardiac Valve Holder; Annal. Thor. Surgery, Apr. 1977, p. 376.

Grismer et al., "A Suture Holder and Separator Attachment to the Starr-Edwards Prosthetic Valve Holders," Surgery, Gynecology and Obstetrics, Mar. 1965, pp. 583-584.

* cited by examiner

HEART VALVE HOLDER ASSEMBLY FOR USE IN VALVE IMPLANTATION PROCEDURES

CROSS-REFERENCE TO RELATED APPLICATIONS

The present application claims priority to U.S. Patent Application No. 60/994,063, filed Sep. 17, 2007, and titled "HEART VALVE HOLDER FOR USE IN VALVE IMPLANTATION PROCEDURES", the entire contents of which is incorporated herein by reference in its entirety.

TECHNICAL FIELD

The present invention relates generally to implantable valvular prostheses, and more particularly relates to a holding system or mechanism that can provide temporary prosthetic heart valve stent post deflection during implantation of valvular prostheses.

BACKGROUND OF THE INVENTION

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, and pulmonary valve). In general terms, however, most prosthetic heart valve designs attempt to replicate the function of the valve being replaced and thus will include valve leaflet-like structures.

As used throughout this specification a "prosthetic heart valve having relatively flexible leaflets" or a "prosthetic heart valve" is intended to encompass bioprosthetic heart valves having leaflets made of a biological material as well as synthetic heart valves having leaflets made of a synthetic (e.g., polymeric) material. Either type of prosthetic heart valve can include a frame or stent or may have no such frame or stent. A stented prosthetic heart valve typically includes a stent having a substantially circular base (or stent ring), around which an annular suture material is disposed for suturing the prosthesis to heart tissue. The stent further typically includes at least two, but typically three, support structures extending from the stent ring. These support structures are commonly referred to as stent posts or commissure posts. These posts typically are rigid yet somewhat flexible structures extending from the stent ring, which are covered by a cloth-like material similar to that of the annular suture material or tissue. The stent or commissure posts define the juncture between adjacent tissue or synthetic leaflets otherwise secured thereto. Examples of bioprosthetic heart valves are described in U.S. Pat. No. 4,106,129 (Carpentier et al.), and U.S. Pat. No. 5,037,434 (Lane), the entire disclosures of which are incorporated herein by reference. These disclosures detail a conventional configuration of three leaflets, with one leaflet disposed between each pair of stent or commissure posts.

Implantation of a stented prosthetic heart valve presents certain technical challenges. For example, a prosthetic mitral valve is normally implanted by placing the prosthesis into the mitral valve annulus with the stent posts projecting blindly deep into the patient's left ventricle. However, due to a lack of visibility through the prosthetic valve, a surgeon can inadvertently loop sutures around the stent posts during suturing of the annular suture ring portion of the prosthesis. Similarly, the extending stent posts may undesirably "snag" on chordae or trabeculae inside the left ventricular cavity. To avoid these complications, various prosthetic valve holders have been designed that inwardly retract or deflect and hold the mitral prosthetic stent posts during implantation. Some of the available prosthetic mitral heart valve holders include an elongated handle and a holder mechanism that is secured to the stent ring and adapted to inwardly deflect the stent posts upon rotation of the handle. An exemplary prosthetic mitral heart valve holder is described in U.S. Pat. No. 4,865,600 (Carpentier et al.), the entire contents of which is incorporated herein by reference. In addition, these concepts can apply to a prosthetic tricuspid valve.

For another example, Medtronic mitral valves are commercially available under the trade designation "Hancock", which valves are mounted to a holder providing a mechanism for inward deflection, as illustrated in the brochures: "A New Dimension—The Hancock II Bioprosthesis", Medtronic Inc., 1991, publication number UC8903226EN and "A New Light on the Hancock Bioprosthesis", Medtronic Inc., 1988, publication number UC8801713EN, both of which are incorporated herein by reference in their entireties. The type of holder described in these publications includes a ratcheting spool attached to the inflow aspect of the valve opposite the stent posts that is rotatable by means of an attached handle to coil lengths of suture, thereby pulling sutures that extend toward the outflow aspect of the valve, through the commissure posts and between the commissure posts, to thereby deflect the commissure posts inward. In general, these prosthetic mitral heart valve holder devices are well-suited for mitral valve replacement because the mitral valve surgical site is relatively easily accessed, with minimal anatomical obstructions on the inflow aspect of the valve. Thus, the surgeon is afforded a large, unobstructed area for locating and maneuvering the handle as well as performing necessary procedural steps (e.g., suturing the annulus suture ring to the heart tissue) with minimal or no interference from the handle and/or mechanism.

Aortic and pulmonic prosthetic heart valve implantation, however, presents different constraints from those associated with mitral or tricuspid valve replacement because there is less room for the surgeon to maneuver during the surgery. With the increased use of minimally invasive heart valve surgery and depending on the type of thoracotomy performed, the surgeon may first have to pass a prosthesis through a small incision in the chest wall of the patient, either through the sternum or between the ribs. Additionally, depending upon the type of aortotomy performed, the surgeon may have to pass the prosthesis through the sinotubular junction, which is typically smaller than the tissue annulus onto which the prosthetic heart valve will be sutured. Because the stent posts extend proximally toward the surgeon in aortic and pulmonic valve replacement (as opposed to the distal stent post direction associated with mitral and/or tricuspid valve replacement), the chances of inadvertently looping sutures about stent post(s) is minimal. However, the proximally extending stent posts associated with the stented prosthesis still can interfere with the various other maneuvers required of the surgeon.

In light of the above, it can be desirable to inwardly deflect the stent posts during implantation of the aortic and/or pulmonic prosthetic heart valve. Unfortunately, the above-described mitral and tricuspid prosthetic heart valve holders are of little value for aortic and pulmonic valve replacement procedures in that these holders position the holder and handle to extend in a direction opposite from that of the stent posts. As such, the holder and handle would have to be removed in order to implant the aortic prosthetic heart valve. Certain approaches have been taken to correct this incompatibility by reconfiguring the holder and handle to extend in a direction similar to the stent posts on the outflow side of the valve, as described, for example, in U.S. Pat. No. 5,476,510 (Eberhardt et al.) and U.S. Pat. No. 5,716,410 (Eberhardt et al.), the entire disclosures of which are incorporated herein by reference.

There is a continued need to provide different devices for assisting in the implantation of stented prosthetic heart valves that can be used in any area of the heart, including devices that can be used for implantation of aortic prosthetic heart valves. In particular, a need exists for a stent post deflection device that is simple and effective to use for areas of the heart that are typically difficult to access by the surgeon, such as for aortic heart valve replacement.

SUMMARY OF THE INVENTION

The present invention is directed to a valve holder assembly that is attachable to a bioprosthesis to assist a surgeon during implantation of a heart valve. In particular, the valve holder of the invention can be used for aortic valve replacement, and provides for temporary deflection of stent posts of the prosthesis, such as an aortic prosthetic heart valve. This deflection of the stent posts helps to ease the implantation process, and also increases the space available for the surgeon to manipulate the sutures and tie suture knots. Other benefits include, but are not limited to: reduced cardiopulmonary bypass time; reduced potential for injury to patient's aorta during knot tying; the ability to implant a properly sized valve and the resultant hemodynamic benefit; increased visibility to knots and a resultant reduction in potential for paravalvular leakage; and potential for less damage to the prosthetic valve during knot tying due to insufficient access.

In one aspect of the invention, a valve holder assembly is provided that includes three separate ratchet sutures for distributing the stresses involved with winding the sutures around a rotor to inwardly deflect three commissure posts of a prosthetic heart valve. This stress distribution can help to prevent or minimize the occurrences of suture breakage during ratcheting of the rotor to deflect the stent posts inward, and also during the process of implanting the prosthetic valve into a patient. In order to accomplish this stress distribution, the rotor and its associated holder are provided with structure that includes a number of specifically positioned holes for a certain path for suture routing. In at least one aspect of the invention, the total number of sutures used for both attaching a holder to a stent ring and for attaching commissure posts to a rotor for deflection of the posts is equal to the number of commissure posts. Typically, the number of commissure posts is three, although there can be more or less than three commissure posts. In addition, in at least some of the embodiments of the invention, the height and leg profile are configured to minimize the overall size of the valve holder assembly. The valve holder assemblies can further be provided with features to minimize or prevent rotor wobble within the holder of a valve holder assembly, and to minimize or prevent "spinning" of the handle relative to the valve holder assembly to which it is mounted.

In another aspect of the invention, a valve holder assembly is provided that includes a prosthetic valve having a stent comprising a stent ring and multiple commissure posts extending from the stent ring, where the valve holder assembly comprises a holder and a rotor. The holder includes a base ring having a central opening, a plurality of legs extending in a generally downward direction from the base ring, each of the plurality of legs comprising a proximal end and a distal end, and at least one flexible finger extending in a generally downward direction from the base ring, wherein the distal end of each of the legs is engageable with the stent ring between adjacent commissure posts. The rotor is positioned within the central opening of the base ring, and comprises a proximal end, a distal end, a circumferential groove adjacent to the distal end of the rotor and a plurality of ratchet teeth spaced from each other around at least a portion of the groove, wherein the at least one finger of the holder is engaged with the circumferential groove of the rotor.

In another aspect of the invention, a valve holder assembly is provided that includes a holder, a rotor, and a handle extending from the rotor. The holder comprises a base ring having a central opening, a plurality of legs extending in a generally downward direction from the base ring, and at least one flexible finger extending in a generally downward direction from the base ring, wherein a distal end of each of the legs is engageable with the stent ring between adjacent commissure posts. The rotor is positioned within the central opening of the base ring and comprises a proximal end, a distal end, a circumferential groove adjacent to the distal end of the rotor and a plurality of ratchet teeth spaced from each other around at least a portion of the groove, wherein the at least one finger of the holder is engaged with the circumferential groove of the rotor.

In yet another aspect of the invention, a valve assembly is provided that includes a holder, a rotor, and a handle extending from the rotor. The holder comprises a base ring having a central opening, a top side that faces in a direction that is generally opposite the downward direction that the plurality of legs extend, a recessed portion on the top side, and a plurality of legs extending in a generally downward direction from the base ring. A distal end of each of the legs is engageable with the stent ring between adjacent commissure posts. The rotor is positioned within the central opening of the base ring and comprises a proximal end, a distal end, and at least one ratchet arm at the proximal end of the rotor, wherein the at least one ratchet arm of the rotor is positioned in the recessed portion of the base ring. The recessed portion of the base ring can further comprise a stop element that is positioned to contact one ratchet arm of the rotor for limiting rotation of the rotor to less than one full rotation of the rotor. The valve holder assembly further comprises a first suture member that comprises a first end attached to the rotor, a second end attached to a first leg of the holder adjacent the proximal end of the first leg, and an elongated suture portion between the first and second suture ends, wherein the elongated suture portion follows a suture path that extends from the rotor to the proximal end of a second leg of the holder, to a first commissure post that is positioned between the first and second legs, to the proximal end of the first leg, to the distal end of the first leg, and to the second suture end at the proximal end of the first leg. In this way, a single piece of suture material provides the functions of attaching the holder to the stent ring and also attaching to a commissure post for deflecting the post when the rotor is rotated relative to the holder.

BRIEF DESCRIPTION OF THE DRAWINGS

The invention will be further explained with reference to the appended Figures, wherein like structure may be referred to similarly throughout the several views, and wherein.

DETAILED DESCRIPTION

Figure 1:
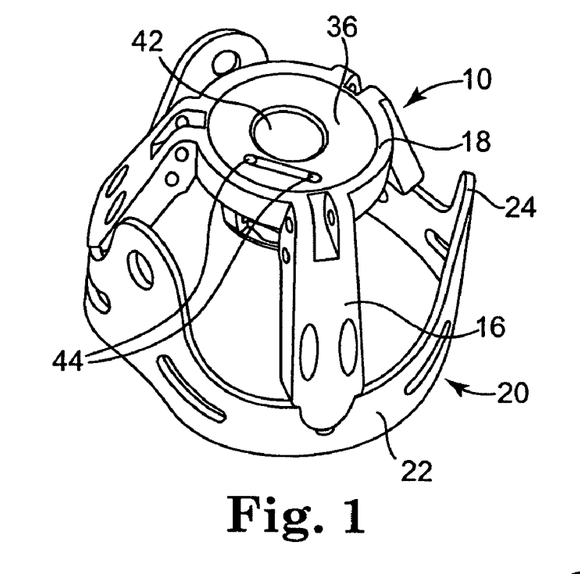
FIG. 1 is a perspective view of one embodiment of a valve holder assembly of the invention, where the valve holder assembly is shown as positioned relative to a frame of a prosthetic heart valve.
Figure 2:
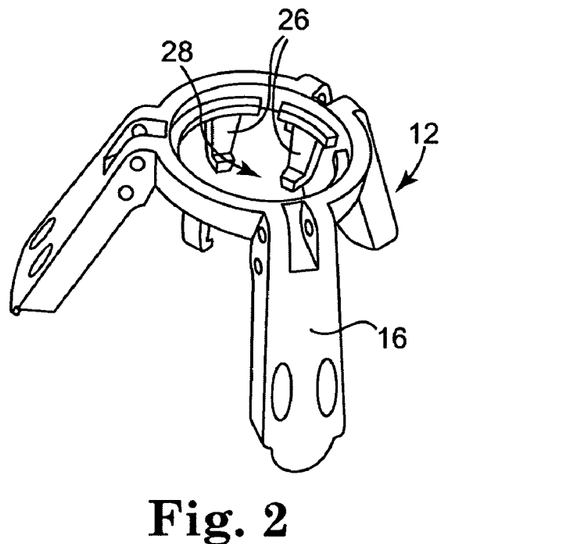
FIG. 2 is a perspective view of a holder of the assembly of FIG. 1.
Figure 3:
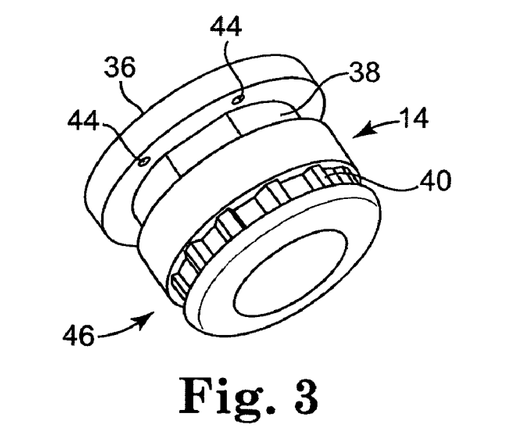
FIG. 3 is a bottom perspective view of a rotor of the assembly of FIG. 1.

Referring now to the Figures, wherein the components are labeled with like numerals throughout the several Figures, and initially to FIGS. 1-3, one embodiment of a valve holder assembly 10 is illustrated, which generally includes a holder 12 and a rotor 14. Holder 12 includes three legs 16 extending from a base ring 18, where FIG. 1 shows the holder 12 positioned relative to a stent frame of an exemplary prosthetic heart valve 20, which may be an aortic valve, for example. Heart valve 20 includes a stent ring 22 from which three commissure posts 24 extend. For clarity of illustration, the cloth fabric and tissue material that make up the valve portion of the assembly (including the leaflets of the valve) are not shown in these figures. Each of the three legs 16 of the holder 12 are shown as positioned with their distal ends on the stent ring 22 between two adjacent commissure posts 24.

The holder 12 further includes three snap-fit fingers 26 that extend downwardly from the base ring 18, although it is contemplated that more or less than three of such fingers 26 are provided. These fingers 26 are preferably relatively flexible toward and away from a longitudinal axis that extends through a center opening 28 of the base ring 18. The fingers 26 are also designed to be engageable with teeth of the rotor 14, as will be described below.

Rotor 14 includes a generally cylindrical shaped body that is sized and shaped to be positioned within the center opening 28 of the base ring 18 and so that it can rotate relative to the holder 12. In particular, the rotor 14 is provided at its proximal end with a first surface 36 that will preferably be positioned so that it is relatively flush with the top surface of the base ring 18 of the holder 12, as shown in FIG. 1, although it is contemplated that the surface 36 be at least slightly recessed or raised relative to the top surface of the base ring 18. The rotor 14 is further provided with a channel 38 that extends around its periphery and is at least slightly spaced from the first surface 36. This channel 38 is sized to accept one or more suture knots (not shown) that will be positioned in this space when a suture is routed through two suture holes 44 and knotted in the area of the channel 38. The rotor 14 also includes a series of ratchet teeth 40 located in a ratchet channel 46 around its periphery near its distal end, which are designed for engagement with the snap-fit fingers 26 of the holder 12. Each of the ratchet teeth 40 has a ramped surface for positive engagement with the snap-fit fingers 26 and to allow rotation of the rotor 14 in only one direction. That is, the snap-fit fingers 26 act to capture the rotor 14 and also as a type of ratcheting limiter to provide a set number of specified positions of the rotor 14 as it is rotated, and also to prevent movement in a direction opposite from the direction of tightening a ratchet suture that is attached to it.

In order to attach the valve holder assembly 10 to the stent ring 22 of the heart valve 20, three separate sutures are provided, which may be referred to as "holder sutures". Each of these sutures is threaded through a series of holes at the distal and proximal ends of the legs 16, and through a cloth or other material that covers the stent ring 22. In order to pull the commissure posts 24 toward the center of the heart valve 20 and to their deflected positions, a ratchet suture is attached to the rotor 14 and through certain holes provided in the holder 12. In operation, the rotor 14 can be rotated relative to the holder 12 via a handle (not shown) that can be attached to or within a central opening 42 of the rotor. During rotation, the snap-fit fingers 26 can simultaneously flex toward or away from the central axis that extends through the center opening 28 of the base ring 18 as they move along the ramped surfaces of the ratchet teeth 40 until they move over the end of each ramped surface and to the start of the next ramped surface. Thus, the ratchet teeth 40 and the snap-fit fingers 26 are preferably designed for cooperative engagement with each other (i.e., it is preferable that each snap-fit finger is positioned in a similar relative location along a ratchet tooth as the other snap-fit fingers of that particular holder). In this way, the valve holder assembly 10 will be relatively stable and free from "wobble" between the holder 12 and its rotor 14 when these components are assembled.

Figure 4:
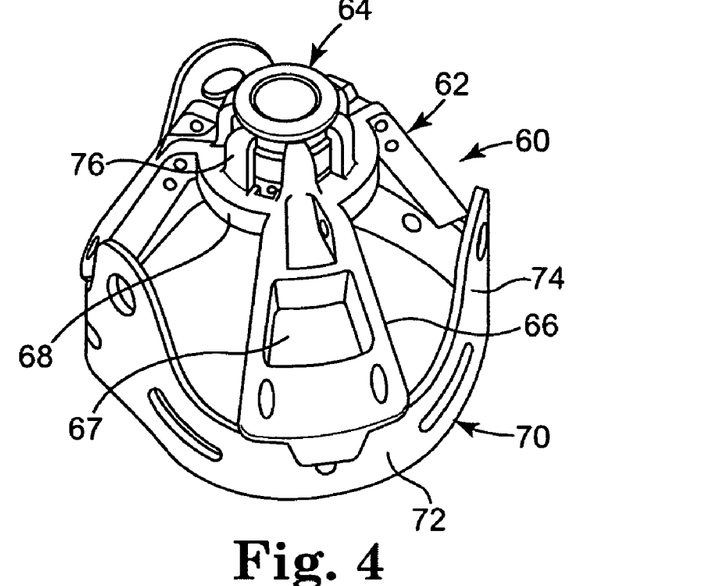
FIG. 4 is a perspective view of another embodiment of a valve holder assembly of the invention, where the valve holder assembly is shown as positioned relative to a frame of a prosthetic heart valve with the stent posts of the heart valve in their undeflected positions.
Figure 5:
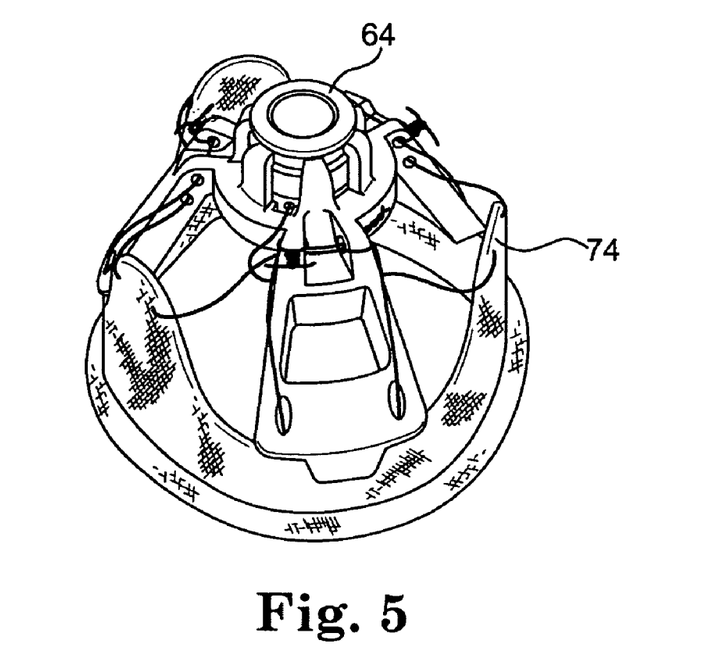
FIG. 5 is a perspective view of the valve holder assembly of FIG. 4, where the valve holder assembly is attached to a prosthetic heart valve with sutures.

FIGS. 4 and 5 illustrate another exemplary embodiment of a valve holder assembly 60 in accordance with the invention, which generally includes a holder 62 and a rotor 64. Again, the holder 62 includes three legs 66 extending from a base ring 68, where FIGS. 4 and 5 both illustrate the holder 62 positioned relative to an exemplary frame of a prosthetic heart valve 70. Heart valve 70 includes a stent ring 72 from which three commissure posts 74 extend. For clarity of illustration, the fabric and tissue material that make up the valve portion of the assembly are not shown in these figures. Each of the three legs 66 of the holder 62 are shown as positioned with their distal ends on the stent ring 72 between two adjacent commissure posts 74. The widths of the legs 66 are tapered at least somewhat from the base ring 68 toward their distal ends so that their distal ends are at least slightly wider than the width of the legs near the base ring 68. This relatively wide portion of the legs 66 can provide additional stability to the assembly 10, while also providing additional protection to the tissue or valve material that is positioned within the heart valve.

The holder 62 further includes multiple snap-fit fingers 76 that extend from the base ring 68 in an upward direction (i.e., in a direction that is opposite the direction from which the legs 66 extend from the base ring 68). The number of snap-fit fingers 76 provided is preferably sufficient to allow for smooth movement of the rotor 64 relative to the holder 62 with which it will be engaged, as will be described below. As shown, each of the snap-fit fingers 76 has a relatively L-shaped configuration for capturing a ridge or groove of the rotor 64 when it is moved into place by pressing the rotor 64 upwardly until a top surface of the rotor engages with the snap-fit fingers 76. The bottom surface of the base ring 68 includes a surface with ratchet teeth around its periphery (not shown) for engagement with a feature of the rotor 64 that is described below.

Rotor 64 includes a generally cylindrical shaped component that is sized and shaped to be positioned within the central opening of the holder 62 and so that it can rotate relative to the holder 62. Rotor 64 is provided near its proximal end with a groove around its periphery that can accept the end of the snap-fit fingers 76 and keep the rotor 64 securely positioned relative to the holder 62. The rotor 64 is further provided with multiple ratchet arms on its bottom side (not shown) that can engage with the ratchet teeth on the bottom surface of the base ring 68. These ratchet teeth preferably allow the rotor 64 to rotate in only one direction, and are configured so that the arms can lock or "click" relative to each of the ratchet teeth until the rotor reaches its desired position. In particular, the holder assembly 60 is sutured to the stent ring 72 and commissure posts 74 in such a way that rotation of the rotor 64 will move the commissure posts 74 from their undeflected positions toward their desired deflected positions for use in a heart valve implantation procedure. One exemplary suture pattern is illustrated in FIG. 5, which includes three "holder sutures" for attaching the valve holder assembly to the stent ring and at least one "ratchet suture" attached to the commissure posts for pulling the commissure posts toward their deflected positions.

Figure 6:
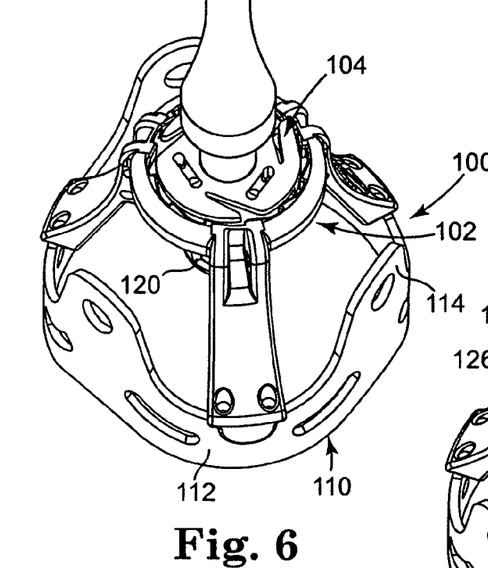
FIG. 6 is a perspective view of another embodiment of a valve holder assembly of the invention with an attached handle, where the valve holder assembly is shown positioned relative to a frame of a prosthetic heart valve.
Figure 7:
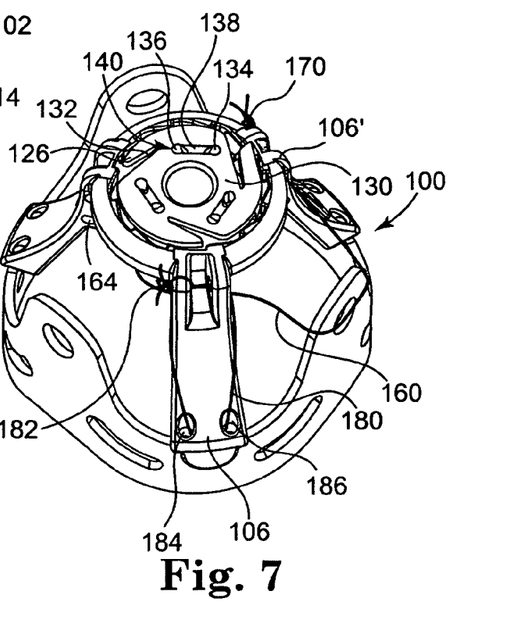
FIG. 7 is another perspective view of the valve holder assembly of FIG. 6, further including a first piece of suture attached to the prosthetic heart valve.
Figure 8:
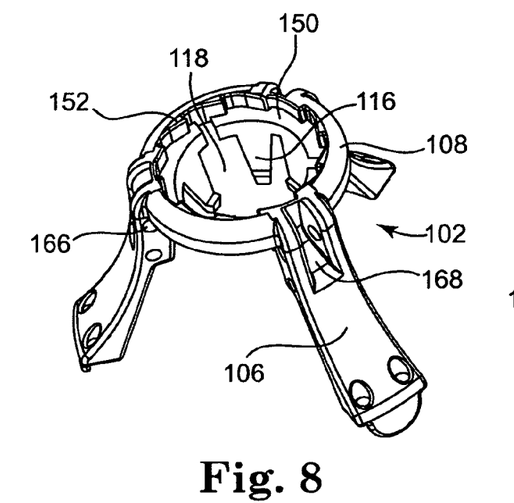
FIG. 8 is a perspective view of a holder of the valve holder assembly of FIGS. 6 and 7.
Figure 9:
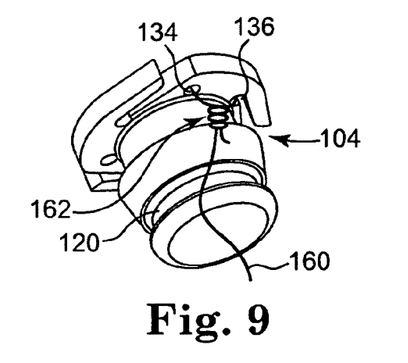
FIG. 9 is a perspective view of a rotor of the valve holder assembly of FIGS. 6 and 7 and further illustrating an exemplary attachment of a piece of suture material.

FIGS. 6-7 illustrate another exemplary embodiment of a valve holder assembly 100 in accordance with the invention, which generally includes a holder 102, which is illustrated separately in FIG. 8, and a rotor 104, which is illustrated separately in FIG. 9. The holder 102 includes three legs 106 extending from a base ring 108, where FIGS. 6 and 7 both illustrate the holder 102 positioned relative to an exemplary prosthetic heart valve 110. Heart valve 110 includes a stent ring 112 from which three commissure posts 114 extend. Each of the three legs 106 of the holder 102 are shown as positioned with their distal ends on the stent ring 112 between two adjacent commissure posts 114. The holder 102 further includes multiple snap-fit fingers 116 that extend generally downwardly from the base ring 108, wherein it is contemplated that at least three of these fingers 116 are preferably provided for stability of the assembly, although it is possible that less than three fingers 116 are provided or that more than three fingers are provided, as is shown in the embodiment of FIG. 8, which includes six fingers 116. These fingers 116 are preferably relatively flexible for movement toward and away from a longitudinal axis that extends through a central opening 118 of the base ring 108. The fingers 116 are also designed for engagement with a groove in a surface of the rotor 104, as will be described below. The fingers 116 are shown as having an extension or hook portion at their distal ends, although any configuration that will provide adequate engagement between the fingers 116 and a groove or other structural feature of the rotor 104 is contemplated.

Rotor 104 includes a generally cylindrical shaped body that is sized and shaped to be positioned securely within the central opening 118 of the holder 102 and to be rotatable relative to the holder 102. The body of rotor 104 is provided near its distal end with a groove 120 around its periphery that can accept the distal end of the fingers 116 and keep the rotor 104 securely positioned relative to the holder 102. The cylindrical body of the rotor 104 is preferably provided with at least a slight taper from its proximal toward its distal end such that the rotor 104 can be moved into the central opening 118 from the top side without damaging or interfering with the attached sutures, such as suture 160 shown in FIG. 9. The rotor 104 can be pressed downwardly until the fingers 116 move at least slightly outward and the ends of the fingers 116 engage within the groove 120, thereby allowing the fingers 116 to move slightly inward and back toward a central longitudinal axis of the valve holder assembly 100. This assembly of the rotor to the holder provides greater stability to the unit because any force transferred to the valve holder assembly by a surgeon (such as via a handle attached to the rotor) will serve to more positively press the components into secure engagement with each other, rather than tending to pull them apart from each other.

The rotor 104 is further provided with multiple ratchet arms 126 at its proximal end, where three of such ratchet arms 126 are illustrated in this embodiment, which will coincide with the number of ratchet sutures that will be used for the valve holder assembly 100. The arms 126 are radially arranged about the proximal end of the rotor 104, and each of the arms 126 are spaced from a central body portion 130 of the rotor 104 by a gap 132. The rotor 104 further includes three slots 140, each of which includes a first through-hole or aperture 134 at one end, a second through-hole or aperture 136 spaced from the first aperture 134, and a channel 138 between the first and second apertures 134, 136. The apertures 134, 136 are preferably sized to accept a piece of suture material, and the channel 138 can be a recessed area in which the suture that extends between the apertures can be positioned. In this way, when a suture extends from aperture 134 to aperture 136, it will be positioned within the channel 138 so that it is relatively flush or slightly recessed with respect to the top surface of the rotor. This placement of the suture can prevent or minimize the possibility of the suture being inadvertently cut during the implantation procedure.

Referring again to FIG. 8, the top surface of the base ring 108 includes a recessed portion 150 that extends around the periphery of its central opening 118. The recessed portion 150 includes multiple teeth 152, which are designed to engage with the ratchet arms 126 of the rotor 104. Each of the teeth 152 has a ramped or sloped surface for positive engagement with the ratchet arms 126 and to allow rotation of the rotor 104 in only one direction. In this way, the teeth 152 act as a type of ratcheting limiter to provide a set number of specific positions of the rotor 104 as it is rotated, and also to prevent movement in a direction opposite from the direction of tightening one or more ratchet sutures that are attached to it. That is, the teeth 152 allow the rotor 104 to rotate in only one direction, where the teeth 152 are preferably configured so that the ratchet arms 126 can lock or "click" relative to each of the teeth 152 as the rotor 104 is turned. Notably, the ratchet arms 126 are spaced longitudinally from the snap-fit fingers 116 along the length of the rotor 104 when the rotor 104 and holder 102 are assembled.

In order to attach the valve holder assembly 100 to a stent of a heart valve, such as a heart valve of the type designated by reference numeral 110, a number of different sutures can be used. One arrangement of sutures utilizes three sutures that are provided for the ratcheting or stent deflecting function by attachment to the commissure posts of the heart valve 110 (referred to herein as "ratchet sutures") and three sutures that are provided mainly for attachment of the valve holder assembly to the heart valve (referred to herein as "holder sutures"). In this way, the stress of deflecting the stent posts is divided over three separate ratchet sutures, rather than all of the stress being taken by a single suture. FIG. 9 illustrates one exemplary attachment of a ratchet suture 160 relative to one of the slots 140. In particular, one end of suture 160 has been passed through first aperture 134, the other end of suture 160 has been passed through second aperture 136, and the two ends of the suture 160 are tied into a knot or series of knots 162 on the lower side of the rotor 104. Two additional ratchet sutures (not shown) will similarly be attached to the other two sets of apertures 134, 136 that are adjacent to the other two ratchet arms 126 and gaps 132. After the sutures are attached to the rotor 104, the rotor 104 can then be inserted into the central opening 118 of the base ring 108 from the top of the holder 102 until the fingers 116 are engaged with the groove 120 of the rotor 104. The loose ends of the sutures 160 will also be inserted through this central opening 118 and into the open area between the legs 106.

Referring again to FIG. 7, one exemplary path for attaching one suture 160 to a commissure post 114 of a stent ring 112 is shown. Although only one suture 160 is illustrated in this Figure, it is understood that one suture 160 would be provided for each of the commissure posts of the stent ring in order to provide the function of generally simultaneously moving these commissure posts inward toward the center of the stent ring. The loose end of the suture 160, which is preferably attached to a needle-type element, is routed from the rotor 104 and through a lower hole 164 positioned on a first leg 106 of the holder 102. The needle-type element is then used to penetrate through a first commissure post 114 and/or through a material that covers the commissure post 114. In this way, the suture 160 is attached to the commissure post 114. The suture 160 is then routed through a set of upper holes 166 positioned on opposite sides of a second leg 106' of the holder 102, where the second leg 106' is spaced circumferentially from the first leg 106. In this way, the suture 160 will extend across a channel 168 that is between the upper holes 166. The suture 160 will then be tied to the second leg 106' adjacent to one of the upper holes 166, such as is illustrated by an exemplary knot 170 in FIG. 7.

As discussed above, this valve holder assembly 100 further includes three holder sutures that are provided mainly for attachment of the valve holder assembly to the heart valve structure. In particular, FIG. 7 illustrates one holder suture 180 that extends through the upper holes 166 of a leg 106, down the leg 106 and through a first leg attachment hole 184. A needle-type element that is attached to the suture 180 is then used to penetrate through the stent ring 112 and/or any fabric material that may be covering it and through a second leg attachment hole 186 that is spaced from the first leg attachment hole 184. The suture 180 is then extended back up the leg 106 to the upper holes 166, where the two ends of the holder suture 180 are stitched, such as is shown by the exemplary knot 182. As with the ratchet suture 160, the holder suture 180 also extends across the channel 168 that is between the upper holes 166.

Figure 15:
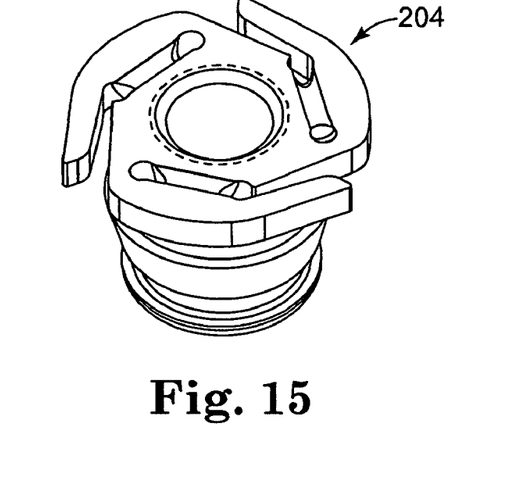
FIG. 15 is a perspective view of a rotor that is provided for use with a holder of the type illustrated in FIGS. 10-14 to make a valve holder assembly.
Figure 16:
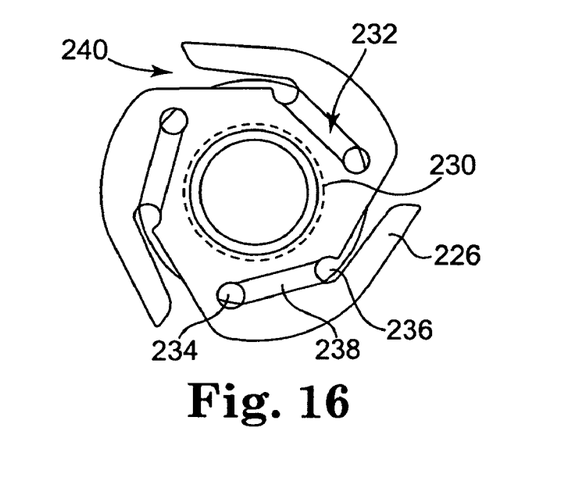
FIG. 16 is a top view of the rotor of FIG. 15.
Figure 17:
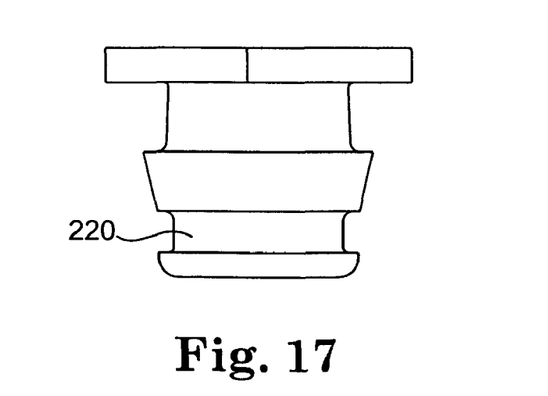
FIG. 17 is a side view of the rotor of FIG. 15.

FIGS. 10-14 illustrate another exemplary embodiment of a holder 202 in accordance with the invention, and FIGS. 15-17 illustrate a rotor 204 that can be used along with holder 202 to make a valve holder assembly. In particular, holder 202 includes three legs 206 extending from a base ring 208. The legs 206 are provided with distal ends that can engage with a stent ring or other feature of a heart valve. The holder 202 further includes three snap-fit fingers 216 that extend downwardly from the base ring 208, wherein it is contemplated that more or less than three fingers 216 can be provided, although it would be more difficult to achieve a stable assembly if too few fingers 216 are provided. These fingers 216 are preferably relatively flexible for movement toward and away from a longitudinal axis that extends through a central opening 218 of the base ring 208. The fingers 216 are also designed to be engageable with a groove 220 of rotor 204, as will be described in further detail below, where the engagement between the components preferably provides an assembly with little to no wobble between its components.

Referring to FIGS. 15-17, rotor 204 includes a generally cylindrical shaped body that is sized and shaped for secure positioning within the central opening 218 of the base ring 208. The body of rotor 204 is provided near its distal end with a groove 220 around its periphery that can accept the distal end of the fingers 216 and keep the rotor 204 securely positioned relative to the holder 202. The cylindrical portion of the rotor 204 is preferably provided with at least a slight taper from the diameter at its proximal end to the diameter at its distal end. In order to assemble the rotor 204 to the holder 202, rotor 204 can be moved into the central opening 218 of base ring 208 from its top side (i.e., the side opposite the direction from which the legs extend) and pressed downwardly until the fingers 216 slide along the outer surface of the rotor 204 and they move or "snap" into the groove 220.

The rotor 204 is also provided with multiple ratchet arms 226 at its proximal end, where three of such ratchet arms 226 are illustrated in this embodiment. The number of ratchet arms will preferably be the same as the number of sutures that will be used for the resultant valve holder assembly, although it is possible that more or less ratchet arms are provided. The arms 226 are radially arranged about the periphery of the proximal end of the rotor 204. Each of the arms 226 are spaced from a central body portion 230 of the rotor 204 by a channel 232 and a slot 240 that extends from one end of the channel 232. Each of the channels 232 includes a first aperture 234 at one end, a second aperture 236 spaced from the first aperture 234, and a recessed portion 238 between the first and second apertures 234, 236, respectively. The slot 240 extends from the second aperture 236 and is "open" such that the arms 226 can flex toward and away from the central body portion 230, thereby changing the width of the slot 240. It is contemplated, however, that the channels 232 instead do not terminate at an open slot 240, but that one or more of the channels 232 instead comprise only an elongated slot portion with apertures at either end. In any case, the apertures are preferably sized to accept a piece of suture material.

Referring again to FIG. 10, the top surface of the base ring 208 includes a recessed portion 250 that extends around the periphery of its central opening 218. The recessed portion 250 includes multiple teeth 252, which are designed to engage with the ratchet arms 226 of the rotor 204. Each of the teeth 252 has a ramped or sloped surface for positive engagement with the ratchet arms 226 and to allow rotation of the rotor 204 in only one direction. In this way, the teeth 252 act as a type of ratcheting limiter to provide a set number of specific positions of the rotor 204 as it is rotated, and also to prevent movement in a direction opposite from the direction of tightening one or more sutures that are attached to it. That is, the teeth 252 allow the rotor 204 to rotate in only one direction, where the teeth 252 are preferably configured so that the ratchet arms 226 can lock or "click" relative to each of the teeth 252 as the rotor 204 is turned.

Figures 10, 11, 12, 13, 14:
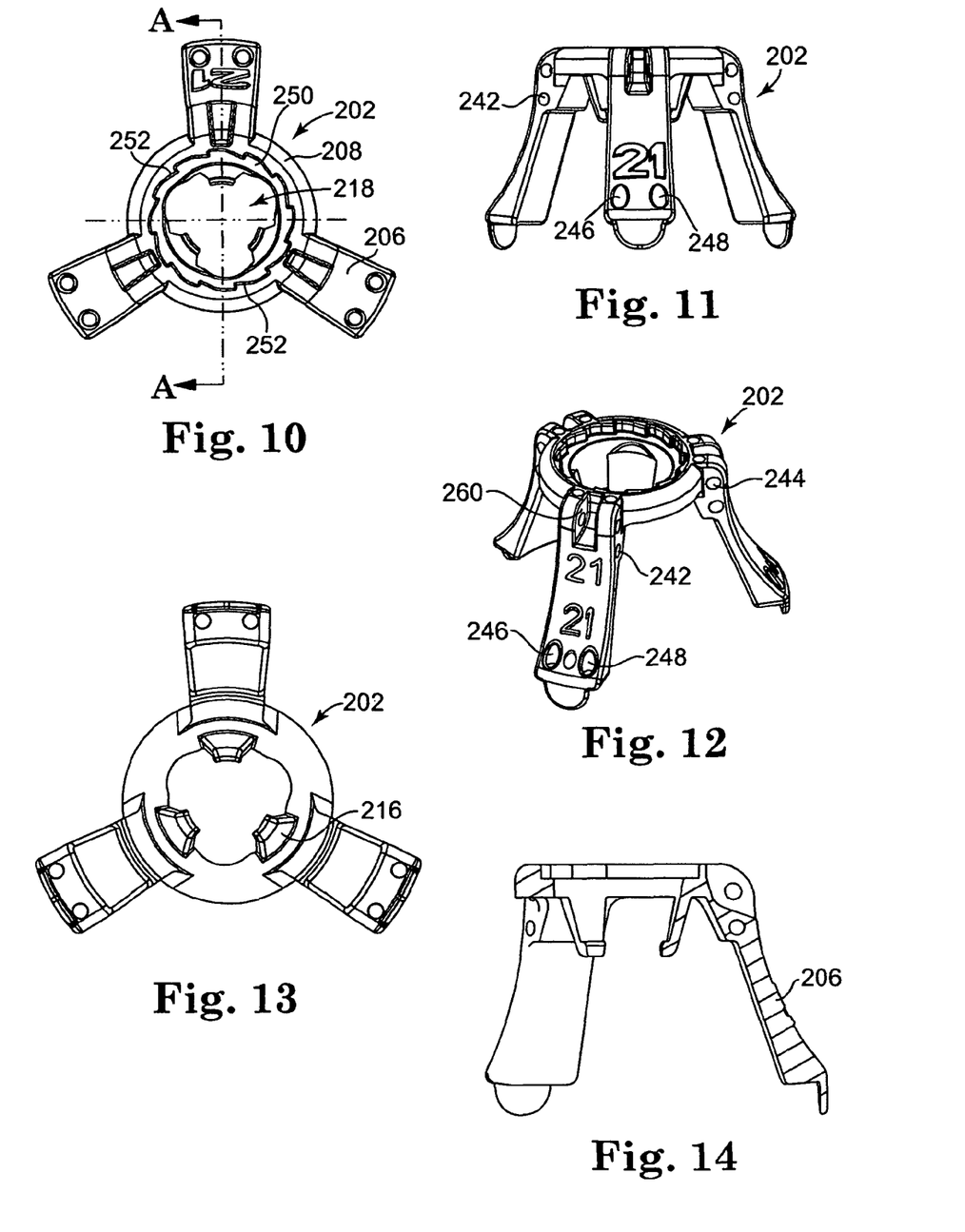
FIG. 10 is a top view of a holder of another embodiment of a valve holder assembly of the invention.
FIG. 11 is a side view of the holder of FIG. 10.
FIG. 12 is a perspective view of the holder of FIG. 10.
FIG. 13 is a bottom view of the holder of FIG. 10.
FIG. 14 is a cross-sectional side view of the holder of FIG. 10, taken along section line A-A.

The valve holder assembly that results from the holder 202 and rotor 204 being attached to each other is an assembly that is attachable to a heart valve using a total of three sutures, thereby eliminating the need to use both three ratchet sutures and three holder sutures for a single assembly. In particular, one exemplary path of a first piece of suture includes tying a piece of suture to one of the channels 232 of the rotor 204, which can be accomplished by extending one end of the suture through a first aperture 234, while the second end of the suture can be moved into a second aperture 236 by moving or sliding it through the open end of a slot 240 until it is positioned in the second aperture 236. The two ends of the suture can then be tied to each other on the bottom side of the rotor 204, thereby creating a secure knot and attaching the suture to the rotor. A needle can be attached to an extending or free end of the suture material and dropped through the central opening 218 of the base ring 208. The rotor 204 can then be pressed into the central opening 218 until the rotor 204 is snapped or secured in place. Although an exemplary path for one suture is described herein, it is understood that this process will be repeated two additional times when one suture is used for each of the three channels 232. That is, three needles with attached sutures can extend through the central opening 218 when the rotor 204 with three channels 232 is attached to the holder 202.

The first piece of suture, as described above, is then routed from the area of the central opening 218 through a bottom hole 242 on a first leg of the holder 202. The suture then is pulled to a tip of a first stent post that is extending from a stent ring of a heart valve and through the fabric on the outside of the post (i.e., between the fabric and the material of the stent post) or through both the post material and the fabric that covers the post. The suture then extends to a second, adjacent leg of the holder 202 and through at least one top hole 244 of that leg. The suture is then extended down along the length of this second leg, through a first hole at the foot of the leg, through the fabric that covers the stent, and then through a second hole at the foot of the leg. The suture is then extended up along the length of the leg and through the bottom hole 242 of that leg. The suture can then be tied off with a knot on one side of a channel 260. In one exemplary suture pattern, the knot is positioned to the right of the area where the suture can be cut when it is desired to remove the holder from the patient and the implanted heart valve. In this way, when the rotor 204 is turned or "ratcheted" to tighten the suture (e.g., a clockwise motion in the illustrated embodiment), the knot will be pulled away from the channel 260 (i.e., the cut point), rather than toward it. The bottom hole 242 of the leg should be large enough to accommodate multiple suture thicknesses, as this hole will be used for the suture path of two pieces of suture material of a particular valve holder assembly.

The above described use of three sutures, each of which generally corresponds to one of the stent posts of a heart valve, can be used in such a way that the force required to deflect the stent posts is distributed relatively evenly among multiple sutures. This can be advantageous over an embodiment that uses a single piece of suture that takes the entire load of deflecting three stent posts. In addition, when these sutures have been subject to ratcheting and are under tension, they further stabilize the holder on the valve for manipulation during the implantation process. The tension in the sutures also makes them easier to cut at specific locations when it is desired to remove the holder from the valve.

Figures 18, 19, 20, 21:
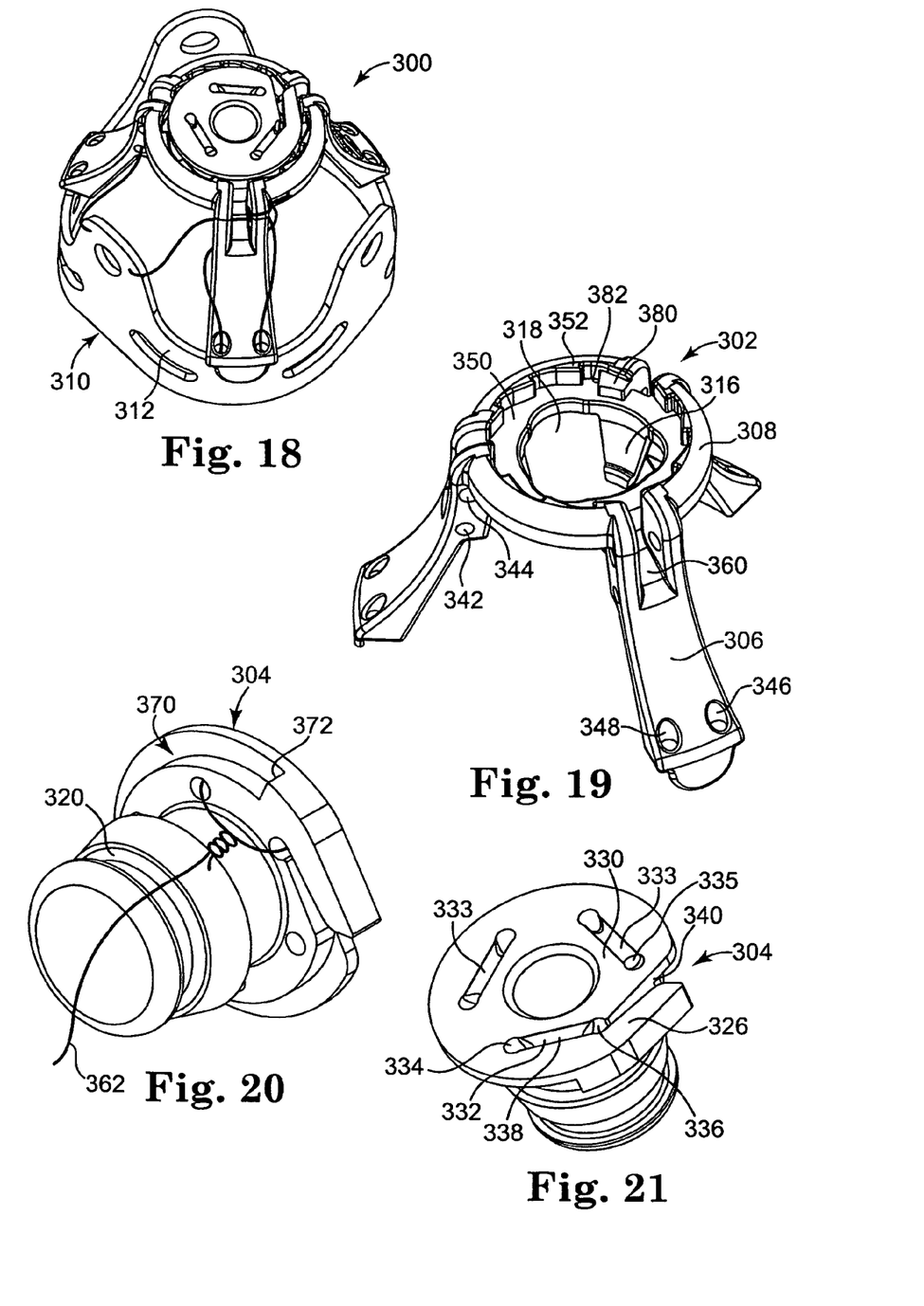
FIG. 18 is a perspective view of another embodiment of a valve holder assembly of the invention, where the valve holder assembly is shown as positioned relative to a frame of a prosthetic heart valve.
FIG. 19 is a perspective view of a holder of the valve holder assembly of FIG. 18.
FIG. 20 is a bottom perspective view of a rotor of the valve holder assembly of FIG. 18.
FIG. 21 is a top perspective view of the rotor of FIG. 20.

FIG. 18 illustrates another embodiment of a valve holder assembly 300, which generally includes a holder 302, which is also illustrated separately in FIG. 19, and a rotor 304, which is also shown separately in FIGS. 20 and 21. Holder 302 is similar in many respects to holders discussed relative to other embodiments of the invention. In particular, holder 302 includes three legs 306 extending from a base ring 308. The legs 306 are provided with distal ends that can engage with a stent ring 312 of a prosthetic heart valve 310. The holder 302 further includes three snap-fit fingers 316 that extend downwardly from the base ring 308, although it is contemplated that more or less than three fingers can be provided. These fingers 316 are preferably relatively flexible for movement toward and away from a longitudinal axis that extends through a central opening 318 of the base ring 308. The fingers 316 are also designed to be engageable with a groove 320 of the rotor 304, as will be described in further detail below.

Referring more specifically to FIGS. 20 and 21, rotor 304 includes a generally cylindrical body that is sized and shaped for secure positioning within the central opening 318 of the base ring 308. The body of rotor 304 is provided near its distal end with a groove 320 around its periphery that can accept the distal end of the fingers 316 and keep the rotor 304 securely positioned relative to the holder 302. The cylindrical portion of the rotor 304 is preferably provided with at least a slight taper from the diameter at its proximal end to the diameter at its distal end. In order to assemble the rotor 304 to the holder 302 to provide the valve holder assembly 300, the rotor 304 can be moved into the central opening 318 of the base ring 308 from its top side and pressed into the opening until the fingers 316 slide along the outer surface of the rotor 304 and they move or "snap" into the groove 320.

The rotor 304 is provided with a single ratchet arm 326 at its proximal end, which is spaced from a central body portion 330 of the rotor 304 by a channel 332 and a slot 340 that extends from one end of the channel 332. Channel 332 includes a first aperture 334 at one end, a second aperture 336 spaced from the first aperture 334, and a recessed portion 338 between the first and second apertures 334, 336. The slot 340 extends from the second aperture 336 and is "open" such that the arm 326 can flex toward and away from the central body portion 330, thereby changing the width of the slot 340. The rotor 304 further includes a groove 370 around a portion of the bottom side of its central body portion 330, the function of which will be described in further detail below. The groove 370 starts generally adjacent to an aperture 335 of a channel 333 and extends around a portion of the periphery and terminates at an end surface 372.

The rotor 304 further includes two channels 333, both of which can be considered "closed" in that no open slot extends from them. These channels 333 each include apertures (e.g., aperture 335) that are spaced from each other by a recessed portion such that a suture may be passed through the apertures with a section of the suture between the apertures positioned in the recessed portion.

Referring again to FIGS. 18 and 19, the top surface of the base ring 308 includes a recessed portion 350 that extends around the periphery of its central opening 318. The recessed portion 350 includes multiple teeth 352, which are designed to engage with the ratchet arm 326 of the rotor 304. Each of the teeth 352 has a ramped or sloped surface for positive engagement with the ratchet arm 326 and to allow rotation of the rotor 304 in only one direction. In this way, the teeth 352 act as a type of ratcheting limiter to provide a set number of specific positions of the rotor 304 as it is rotated, and also to prevent movement in a direction opposite from the direction of tightening one or more sutures that are attached to it. That is, the teeth 352 allow the rotor 304 to rotate in only one direction, where the teeth 352 are preferably configured so that the ratchet arms 326 can lock or "click" relative to each of the teeth 352 as the rotor 304 is turned.

The recessed portion 350 further includes a pad 380 with a stop surface 382. When the rotor 304 is positioned within the central opening of the base ring 308, as illustrated in FIG. 18, the rotor 304 can be rotated so that the ratchet arm 326 moves along the teeth 352 until the end surface 372 of the groove 370 comes into contact with the stop surface 382 of the pad 380. This configuration thereby limits or controls the amount of rotation of the rotor 304 relative to the holder 302. In this particular embodiment, the pad 380 is positioned so that the rotor 304 can rotate slightly less than one full rotation relative to the recessed portion 350 of the holder 302; however, it is contemplated that the pad 380 and the groove 370 of the rotor 304 are configured so that the amount of rotation is different than that shown and described relative to this embodiment.

As with the holder and rotor configurations described above relative to FIGS. 10-17, the valve holder assembly 300 can also be attached to a heart valve using a total of three sutures. That is, a similar suture path may be used for each of the legs 306, where the legs 306 can include the same or similar holes to accept the suture material. In particular, one exemplary path of a first piece of suture 362 includes tying that piece of suture to one of the channels 332 of the rotor 304, which can be accomplished by extending one suture end through aperture 334 and moving the length of suture into the aperture 336 through the open end of the slot 340, with the second end of the suture extending from the aperture 336. The two suture ends can then be tied to each other on the bottom side of the rotor 304, thereby attaching the suture 362 to the rotor 304. A needle can be attached to an extending or free end of the suture material and dropped through the central opening 318 of the base ring 308. The rotor 304 can then be pressed into the central opening 318 until the rotor 304 is snapped or secured in place. Although this path for one exemplary suture 362 is described herein, the same process (along with the subsequent suture steps described below) will be similarly performed with an additional suture piece for each channel 333.

The suture 362 is then routed from the area of the central opening 318 through a bottom hole 342 on a first leg 306 of the holder 302. The suture is then pulled to a tip of a first stent post, which extends from the stent ring 312, and through a fabric/covering on the outside of the stent post or through both the post material and the fabric covering on the outside of the stent post or through both the post material and the fabric that covers the post. The suture 362 then extends to another, adjacent leg of the holder 302 and through a top hole 344 of that leg. The suture is then extended along the length of this leg, through a first hole 346 at the foot of the leg, through the fabric that covers the stent ring 312, and then through a second hole 348 at the foot of the leg. The suture is then extended up along the length of the leg and through the bottom hole 342 of that leg. The suture can then be tied off with a knot, preferably on the right side of a channel 360. This knot positioning is to the right of the area where the suture can be cut to remove the holder from the patient. In this way, when the rotor is turned or "ratcheted" to tighten the suture (e.g., in a clockwise motion in the illustrated embodiment), the knot will be pulled away from the channel 360 (i.e., the cut point), rather than toward it.

As referred to herein, the prosthetic heart valves used with the invention may include a wide variety of different configurations, such as a prosthetic heart valve having tissue leaflets or a synthetic heart valve having polymeric leaflets, and can be specifically configured for replacing any heart valve. That is, while much of the description herein is directed to replacement of aortic valves, the valve holder assemblies of the invention can also generally be used for replacement of pulmonic valves, for use as a venous valve, or to replace a failed bioprosthesis, such as in the area of an aortic valve or mitral valve, for example. In any case, exemplary prosthetic heart valves used with the present invention generally include a stent including a sewing ring from which multiple stent posts or commissure posts extend. All or a portion of the stent, including the sewing ring and stent posts, is preferably covered by a flexible covering, which may be a fabric, polymer, cloth, or tissue material to which leaflets (not shown) of the valve can be sewn. Further, as is known in the art, the internal structure of each of the stent posts or commissure posts is formed of a stiff but resiliently bendable material. This construction allows the stent posts to be deflected by the application of an external force. Once this external force is removed or reduced, the stent posts will then move at least partially back toward their undeflected configuration.

The valve holder assemblies of the invention can further include a handle that is attachable to and detachable from the rotor at a distal end of the handle. In one preferred embodiment, the connection between the handle and rotor is accomplished via a threaded connection, where the end of the handle has outer threads that are compatible for connection with inner threads of a generally central opening in the rotor. However, the handle may be connectable to the rotor in a number of different ways that allow the surgeon to attach and detach these two components with relatively minimal effort, when desired. The handle can be made of stainless steel or another suitably rigid, sterilizable material. A longitudinal axis of the handle can define a central, longitudinal axis of its corresponding holder. Exemplary handle connections can incorporate a pivot joint to enable optimum positioning of the handle and/or use a shape memory material (e.g., nitinol). Another exemplary embodiment of the handle may additionally include a reduced diameter portion along its length for enabling the handle to be bent to a desired angle during the valve implant procedure. Commercially available handles that may be used include those available from Medtronic Inc. of Minneapolis, Minn. under the trade designation "Mosiac" and "Hancock II."

In another embodiment, the rotor to which a handle is attached can include threads that stop short of the bottom that help to prevent or minimize "spinning" of the handle relative to the rotor. In particular, with each use of the handle, the handle threads can cut into the material of the rotor to thereby cut new threads that keep the assembly relatively stable.

The invention further includes a method of installing a prosthetic valve in a patient, the prosthetic valve having a stent comprising a stent base and multiple commissure posts projecting from the stent base. The method comprises the steps of: providing a holder of the invention that comprises a base ring or base member including a plurality of extending legs, a rotor positioned relative to a plurality of teeth within the base ring, and a handle extending from the rotor; attaching each of the extending legs to a stent between adjacent commissure posts; attaching plural sutures to the ratcheting member, the stent ring, and the commissure posts; rotating the ratcheting member by rotation of the handle to deflect the commissure posts inwardly as compared to their undeflected position; positioning the holder with the attached prosthetic valve at an implantation site of a patient; and suturing the prosthetic valve to tissue of the patient. The prosthetic valve may be an aortic prosthetic heart valve. The method may also include the steps of detaching the valve from the holder and removing the holder from the patient.

The present invention has now been described with reference to several embodiments thereof. The entire disclosure of any patents, patent applications, publications and journal articles identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A valve holder assembly for a prosthetic valve having a stent comprising a stent ring and multiple commissure posts extending from the stent ring, the valve holder assembly comprising:
    a holder comprising:
        a base ring having a central opening;
        a plurality of legs extending in a generally downward direction from the base ring, each of the plurality of legs comprising a proximal end and a distal end; and
        at least one flexible finger extending in a generally downward direction from the base ring,
        wherein the distal end of each of the legs is engageable with the stent ring between adjacent commissure posts;
    a rotor positioned within the central opening of the base ring, the rotor comprising a proximal end, a distal end, a circumferential groove adjacent to the distal end of the rotor, and at least one ratchet arm at the proximal end of the rotor, wherein a portion of the at least one finger of the holder is engaged with the circumferential groove of the rotor; and
    a handle extending from the proximal end of the rotor for rotation of the rotor relative to the holder.

2. The valve holder assembly of claim 1, further comprising a recessed portion in a top side of the base ring, wherein the top side of the base ring faces in a direction that is generally opposite the downward direction that the plurality of legs extend, and wherein the at least one ratchet arm of the rotor is positioned in the recessed portion of the base ring.

3. The valve holder assembly of claim 2, wherein the recessed portion of the base ring comprises a plurality of ratchet teeth that are engageable with the at least one ratchet arm of the rotor.

4. The valve holder assembly of claim 1, wherein each of the at least one ratchet arms is spaced from a central body portion of the rotor by a gap having a width.

5. The valve holder assembly of claim 4, wherein each of the at least one ratchet arms is flexibly moveable toward and away from the central body portion of the rotor when the rotor is rotated relative to the holder to thereby change the width of the gap.

6. The valve holder assembly of claim 5, wherein the recessed portion of the base ring further comprises a stop element that is positioned to contact one of the at least one ratchet arms of the rotor for limiting rotation of the rotor relative to the holder to less than one full rotation of the rotor.

7. The valve holder assembly of claim 1, further comprising three ratchet arms at the proximal end of the rotor.

8. The valve holder assembly of claim 7, wherein the proximal end of the rotor further comprises three slots, wherein each slot is circumferentially positioned between two ratchet arms.

9. The valve holder assembly of claim 8, wherein each of the slots comprises a first aperture, a second aperture spaced from the first aperture, and a recessed channel portion between the first and second apertures.

10. The valve holder assembly of claim 1, wherein each leg of the holder comprises at least one upper aperture and at least one lower aperture at its proximal end, and wherein each leg of the holder comprises at least one leg attachment aperture at its distal end.

11. The valve holder assembly of claim 1, wherein each of the at least one flexible fingers is moveable relative to a longitudinal axis that extends through the central opening of the base ring for engagement with the circumferential groove of the rotor during assembly of the rotor within the central opening of the base ring.

12. A valve holder assembly for a prosthetic valve having a stent comprising a stent ring and multiple commissure posts extending from the stent ring, the valve holder assembly comprising:
    a holder comprising:
        a base ring having a central opening;
        a plurality of legs extending in a generally downward direction from the base ring, each of the plurality of legs comprising a proximal end and a distal end; and
        at least one flexible finger extending in a generally downward direction from the base ring,
        wherein the distal end of each of the legs is engageable with the stent ring between adjacent commissure posts;
    a rotor positioned within the central opening of the base ring, the rotor comprising a proximal end, a distal end, a circumferential groove adjacent to the distal end of the rotor and comprising a plurality of ratchet teeth spaced from each other around at least a portion of the groove, wherein the at least one finger of the holder is engaged with the circumferential groove of the rotor; and
    a handle extending from the proximal end of the rotor for rotation of the rotor relative to the holder.

13. The valve holder assembly of claim 12, wherein the proximal end of the rotor comprises a first suture hole, a second suture hole spaced from the first suture hole, and a recessed channel between the first and second suture holes.

14. A method of implanting a prosthetic valve in a patient, the prosthetic valve including a stent comprising a stent ring and multiple commissure posts extending from the stent ring, the method comprising the steps of:
    providing a valve holder assembly comprising:
        a holder comprising a base ring having a central opening, a plurality of legs extending in a generally downward direction from the base ring, each of the plurality of legs comprising a proximal end and a distal end, wherein the distal end of each of the legs is engageable with the stent ring between adjacent commissure posts, and at least one flexible finger extending in a generally downward direction from the base ring;
        a rotor positioned within the central opening of the base ring, the rotor comprising a proximal end, a distal end, and at least one ratchet arm at the proximal end of the rotor, wherein a portion of the at least one finger of the holder is engaged with the circumferential groove of the rotor; and a handle extending from the proximal end of the rotor for rotation of the rotor relative to the holder;

attaching the valve holder assembly to the stent of the prosthetic valve using a plurality of suture members;

rotating the rotor relative to the holder to generally simultaneously deflect the multiple commissure posts of the stent inwardly;

positioning the valve holder assembly with the attached prosthetic valve in an implantation site of a patient;

attaching the prosthetic valve to the tissue of the patient;

detaching the prosthetic valve from the valve holder assembly; and removing the valve holder assembly from the patient.

15. The method of claim 14, wherein the number of commissure posts is the same as the number of suture members used for attaching the valve holder assembly to the stent, wherein each suture member is attached to the rotor, at least a portion of two adjacent legs of the plurality of legs, and one of the multiple commissure posts.

16. The method of claim 14, wherein a first suture member comprises a first end attached to the rotor, a second end attached to a first leg of the holder adjacent the proximal end of the first leg, and an elongated suture portion between the first and second suture ends, wherein the elongated suture portion follows a suture path that extends from the rotor to the proximal end of a second leg of the holder, to a first commissure post that is positioned between the first and second legs, to the proximal end of the first leg, to the distal end of the first leg, and to the second suture end at the proximal end of the first leg.

17. A valve holder assembly for a prosthetic valve having a stent comprising a stent ring and multiple commissure posts extending from the stent ring, the valve holder assembly comprising:

a holder comprising:

a base ring having a central opening, a top side that faces in a direction that is generally opposite the downward direction that the plurality of legs extend, and a recessed portion on the top side; and a plurality of legs extending in a generally downward direction from the base ring, each of the plurality of legs comprising a proximal end and a distal end;

wherein the distal end of each of the legs is engageable with the stent ring between adjacent commissure posts;

a rotor positioned within the central opening of the base ring, the rotor comprising a proximal end, a distal end, and at least one ratchet arm at the proximal end of the rotor; and a handle extending from the proximal end of the rotor for rotation of the rotor relative to the holder;

wherein the at least one ratchet arm of the rotor is positioned in the recessed portion of the base ring.

18. The valve holder of claim 17, wherein the recessed portion of the base ring further comprises a stop element that is positioned to contact one ratchet arm of the rotor for limiting rotation of the rotor to less than one full rotation of the rotor.

19. The valve holder assembly of claim 17, wherein the recessed portion of the base ring comprises a plurality of ratchet teeth that are engageable with the at least one ratchet arm of the rotor.

20. The valve holder assembly of claim 17, further comprising a first suture member that comprises a first end attached to the rotor, a second end attached to a first leg of the holder adjacent the proximal end of the first leg, and an elongated suture portion between the first and second suture ends, wherein the elongated suture portion follows a suture path that extends from the rotor to the proximal end of a second leg of the holder, to a first commissure post that is positioned between the first and second legs, to the proximal end of the first leg, to the distal end of the first leg, and to the second suture end at the proximal end of the first leg.

\* \* \* \* \*